United States Patent
Fraidenraich et al.

(10) Patent No.: US 8,802,629 B1
(45) Date of Patent: Aug. 12, 2014

(54) CORRECTIVE ROLES OF INSULIN-LIKE GROWTH FACTOR-BINDING PROTEIN-3 IN CARDIOMYOPATHY

(75) Inventors: Diego Fraidenraich, New York, NY (US); Qingshi Zhao, West Orange, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 13/468,005

(22) Filed: May 9, 2012

Related U.S. Application Data

(60) Provisional application No. 61/483,832, filed on May 9, 2011.

(51) Int. Cl.
*A61P 9/00* (2006.01)
*A61K 38/17* (2006.01)
*C07K 14/435* (2006.01)

(52) U.S. Cl.
USPC ......... 514/16.4; 514/13.3; 514/21.2; 530/350

(58) Field of Classification Search
None
See application file for complete search history.

(56) References Cited

U.S. PATENT DOCUMENTS

| | | |
|---|---|---|
| 7,405,195 B2 | 7/2008 | Chen et al. |
| 2012/0059060 A1 | 3/2012 | Blanda et al. |

OTHER PUBLICATIONS

Zhao et al, 2011. Developmental Biology, 340: 53-64, published on-line Oct. 23, 2010.*
Henson et al, 2000. DNA and Cell Biology, 19(12): 757-763.*
Harry's Cosmeticology, 7th Ed., Edited by Wilkinson et al. (Chemical Publishing, London 1982) (Synopsis only).
Lieberman et al., "Pharmaceutical Dosage Forms—Disperse Systems," Taylor Print on Dema, vol. 1•(1988) & vol. 2 (1989) (Synopsis only).
The Handbook of Cosmetic Science and Technology, 1st Ed. Knowlton & Pearce (Elsevier 1993).
Fraidenraich et al., "Rescue of cardiac defects in Id knockout embryos by injection of embryonic stem cells," Science (2004), vol. 306, pp. 247-252.
Kisanuki et al., "Tie2-Cre transgenic mice: a new model for endothelial cell-lineage analysis in vivo," Dev Biol., (2001) vol. 230, pp. 230-242 (Abstract only).
Nam et al., "High Levels of Id1 Expression Define B1 Type Adult Neural Stem Cells," Cell Stem Cell., (2009) vol. 5, pp. 515-526.
Peter et al., "Inhibition of p38(alpha) MAPK rescues cardiomyopathy induced by overexpressed (beta)2-adrenergic receptor, but not (beta)1-adrenergic receptor," Journal of Clinical Investigation, (2007) vol. 17, pp. 1335-1343.
Yamamoto et al., "Improved Therapeutic Efficacy in Cardiomyocyte Transplantation for Myocardial Infarction with Release System of Basic Fibroblast Growth Factor," Artificial Organs, (2003) vol. 27, pp. 181-184.

* cited by examiner

*Primary Examiner* — Zachary Howard
(74) *Attorney, Agent, or Firm* — Fox Rothschild LLP

(57) ABSTRACT

The invention relates to methods of promoting the expression of pro-angiogenic factors and decreasing the expression of anti-angiogenic and fibrotic factors in a cell, as well as the treatment of cardiomyopathy and wounds.

4 Claims, No Drawings

CORRECTIVE ROLES OF INSULIN-LIKE GROWTH FACTOR-BINDING PROTEIN-3 IN CARDIOMYOPATHY

CROSS-REFERENCE TO RELATED APPLICATION

This application claims priority of U.S. Provisional Application No. 61/483,832 filed on May 9, 2012, the disclosure of which is incorporated herein by reference in its entirety.

FIELD OF THE INVENTION

The invention relates to methods of promoting the expression of pro-angiogenic factors and decreasing the expression of anti-angiogenic and fibrotic factors in a cell, as well as the treatment of cardiomyopathy and wounds.

BACKGROUND OF THE INVENTION

Cardiomyopathy refers to diseases of the heart muscle. In cardiomyopathy, the heart muscle becomes enlarged, thick, or rigid. As cardiomyopathy worsens, the heart becomes weaker. It's less able to pump blood through the body and maintain a normal electrical rhythm. This can lead to heart failure or irregular heartbeats called arrhythmias. In turn, heart failure can cause fluid to build up in the lungs, ankles, feet, legs, or abdomen.

The Id1 and Id3 genes play major roles during cardiac development, despite their expression being confined to non-myocardial layers (endocardium-endothelium-epicardium). Animal models that lack Id1 and Id3 genes exist, and the cardiac phenotype is associated with ventricular septal defects, trabeculation and proliferation defects that result in a marked thinning of the myocardial wall. However, these animal models preclude the study of the roles of Id1 and Id3 in the postnatal heart, due to the lethality of the double knockout. As a result, the impact on the loss of vasculature on the postnatal heart is not known, and thus there is a lack of treatment options for cardiomyopathies associated with a thin myocardial wall. There is a need for new therapies to treat cardiac myopathies associated with the thinning of the myocardial wall.

SUMMARY OF THE INVENTION

In one aspect, the invention provides a method to concurrently promote expression of at least one pro-angiogenic factor and decrease expression of at least one anti-angiogenic factor in a cell comprising contacting a' cell with an effective amount of IGFbp3. The method further provides for the decreased expression of at least one fibrotic factor in said cell. The anti-angiogenic factor may be Thbs1 or Thbs4. The pro-angiogenic factor may be Angpt1. The fibrotic factor also decreases the expression of at least one collagen gene. The cell is at least one myocardial cell or at least one myocyte.

In a second aspect, the invention provides a topical pharmaceutical composition comprising IGFbp3 and a pharmaceutically acceptable carrier.

In a third aspect, the invention provides a method to promote the healing of a wound comprising contacting said wound with an effective amount of IGFbp3. The wound may be skin. The wound may be contacted by topical administration with a topical pharmaceutical composition comprising IGFbp3 and a pharmaceutically acceptable carrier.

In a fourth aspect, the invention provides a method to promote angiogenesis in a subject diagnosed with cardiomyopathy comprising administration to said subject an effective amount of IGFbp3. The cardiomyopathy may be dilated cardiomyopathy.

In a fifth aspect, the invention provides a method to treat cardiomyopathy in a subject in need of such treatment comprising administration to said subject an effective amount of IGFbp3. The cardiomyopathy may be dilated cardiomyopathy.

DETAILED DESCRIPTION OF THE INVENTION

1. Definitions

The terms "polypeptide", "peptide", "protein", and "protein fragment" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "biologically active fragment" is meant a fragment of a full-length parent polypeptide which fragment retains an activity of the parent polypeptide. As used herein, the term "biologically active fragment" includes deletion variants and small peptides, for example of at least 6, 7, 8, 9, 10, 11, 12, 13, 14, 15, 16, 17, 18, 19, 20, 21, 22, 23, 24, 25, 26, 27, 28, 29, 30, 35, 40, 45, 50 contiguous amino acid residues, which comprise an activity of the parent polypeptide. Peptides of this type may be obtained through the application of standard recombinant nucleic acid techniques or synthesized using conventional liquid or solid phase synthesis techniques. For example, reference may be made to solution synthesis or solid phase synthesis as described, for example, in Chapter 9 entitled "Peptide Synthesis" by Atherton and Shephard which is included in a publication entitled "Synthetic Vaccines" edited by Nicholson and published by Blackwell Scientific Publications. Alternatively, peptides can be produced by digestion of a polypeptide of the invention with proteinases such as endoLys-C, endoArg-C, endoGlu-C and staphylococcus V8-protease. The digested fragments can be purified by, for example, high performance liquid chromatographic (HPLC) techniques.

As used herein, the term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

The term "factor" means proteins, endogenously produced substances by a cell that bind to cell surface or nuclear receptors and generally function to promote cell proliferation, maturation, survival, and/or regeneration by activating a number of downstream pathways.

"IGFbp3" generally refers to active Insulin-Like Growth Factor binding protein-3 and biologically active fragments thereof.

Terms such as "treating" or "treatment" or "to treat" or "alleviating" or "to alleviate" refer to both 1) therapeutic measures that cure, slow down, lessen symptoms of, and/or halt progression of a diagnosed pathologic condition or disorder and 2) prophylactic or preventative measures that prevent and/or slow the development of a targeted pathologic condition or disorder. Thus those in need of treatment include those already with the disorder; those prone to have the disorder; and those in whom the disorder is to be prevented, such as cardiomyopathy and the related symptoms or the treatment of a wound.

2. Topical Pharmaceutical Compositions

The present invention provides topical pharmaceutical compositions comprising IGFbp3 and a pharmaceutically acceptable carrier.

The IGFbp3 can be an isolated or purified protein. An "isolated" or "purified" protein refers to protein that has been separated from other proteins, lipids, and nucleic acids with which it is naturally associated. The polypeptide/protein can constitute at least 10% (i.e., any percentage between 10% and 100%, e.g., 20%, 30%, 40%, 50%, 60%, 70%, 80%, 85%, 90%, 95%, and 99%) by dry weight of the purified preparation. Purity can be measured by any appropriate standard method, for example, by column chromatography, polyacrylamide gel electrophoresis, or HPLC analysis. An isolated protein described in the invention can be purified from a natural source, produced by recombinant DNA techniques, or by chemical methods.

The IGFbp3 may also be pegylated to improve the half life and stability. The IGFbp3 may also be conjugated to biodegradable polymers to improve the stability of the factor, as well as for sustained release delivery of the pharmaceutical composition.

"Biodegradable" for the purposes of this invention means the ability of any biocompatible material to breakdown within the physiological environment of the wound or target area by one or more physical, chemical, or cellular processes at a rate consistent with providing structural or pharmaceutical barriers (or both) at a therapeutic level controllable by selection of a polymer or mixture of polymers (also referred to as polymeric materials), including, but not limited to: polylactide polymers (PLA), copolymers of lactic and glycolic acids (PLGA), polylactic acid-polyethylene oxide copolymers, poly($\epsilon$.-caprolactone-co-L-lactic acid (PCL-LA), glycine/PLA copolymers; PLA copolymers involving polyethylene oxides (PEO), acetylated polyvinyl alcohol (PVA)/polycaprolactone copolymers, hydroxybutyrate-hydroxyvalerate copolymers, polyesters such as, but not limited to, aspartic acid and different aliphatic diols, poly(alkylene tartrates) and their copolymers with polyurethanes, polyglutamates with various ester contents and with chemically or enzymatically degradable bonds, other biodegradable nonpeptidic polyamides, amino acid polymers, polyanhydride drug carriers such as, but not limited to, poly(sebacic acid) (PSA), aliphatic-aromatic homopolymers, and poly(anhydride-co-imides), poly(phosphoesters) by matrix or pendant delivery systems, poly(phosphazenes), poly(iminocarbonate), crosslinked poly(ortho ester), hydroxylated polyester-urethanes, or the like. The polymer can be a gel or hydrogel type polymer, PLA or PLGA polymer or mixtures or derivatives thereof.

The topical pharmaceutical composition comprising the IGFbp3 and pharmaceutically acceptable carrier, may be in the form of biodegradable polymeric implants, non-biodegradable polymeric implants, biodegradable polymeric microparticles, and combinations thereof. Implants may be in the form of rods, wafers, sheets, filaments, spheres, and the like. Particles are generally smaller than the implants disclosed herein, and may vary in shape. For example, certain embodiments of the present invention utilize substantially spherical particles. These particles may be in the form of microspheres. Other embodiments may utilize randomly configured particles, such as particles that have one or more flat or planar surfaces. The drug delivery system may comprise a population of such particles with a predetermined size distribution. For example, a major portion of the population may comprise particles having a desired diameter measurement. Additional sustained release delivery biodegradeable polymer, microparticle and implant formulations are described in U.S. Patent Publication No. 2012/0059060.

Examples of pharmaceutically acceptable carriers or additives include water, a pharmaceutical acceptable organic solvent, collagen, polyvinyl alcohol, polyvinylpyrrolidone, a carboxyvinyl polymer, carboxymethylcellulose sodium, polyacrylic sodium, sodium alginate, water-soluble dextran, carboxymethyl starch sodium, pectin, methyl cellulose, ethyl cellulose, xanthan gum, gum Arabic, casein, gelatin, agar, diglycerin, glycerin, propylene glycol, polyethylene glycol, Vaseline, paraffin, stearyl alcohol, stearic acid, human serum albumin (HSA), mannitol, sorbitol, lactose, a pharmaceutically acceptable surfactant and the like. Additives used are chosen from, but not limited to, the above or combinations thereof, as appropriate, depending on the dosage form of the present invention.

Pharmaceutical compositions for topical administration according to the present invention can be formulated as solutions, ointments, creams, suspensions, lotions, powders, pastes, gels, sprays, aerosols, or oils. Alternatively, topical formulations can be in the form of patches or dressings impregnated with active ingredient(s), which can optionally comprise one or more excipients or diluents. In some preferred embodiments, the topical formulations include a material that would enhance absorption or penetration of the active agent(s) through the skin or other affected areas.

A topical composition contains a safe and effective amount of a dermatologically acceptable carrier suitable for application to the skin. A "cosmetically acceptable" or "dermatologically-acceptable" composition or component refers a composition or component that is suitable for use in contact with human skin without undue toxicity, incompatibility, instability, allergic response, and the like. The carrier enables an active agent (such as IGFbp3) and optional component to be delivered to the skin at an appropriate concentration(s). The carrier can thus act as a diluent, dispersant, solvent, or the like to ensure that the active materials are applied to and distributed evenly over the selected target at an appropriate concentration. The carrier can be solid, semi-solid, or liquid. Preferably, it is in the form of a lotion, a cream, or a gel, in particular one that has a sufficient thickness or yield point to prevent the active materials from sedimenting. The carrier can be inert or possess dermatological benefits of its own. It should also be physically and chemically compatible with the active components described herein, and should not unduly impair stability, efficacy, or other use benefits associated with the composition.

The topical composition may be a cosmetic or dermatologic product in the form known in the art for topical or transdermal applications, including solutions, aerosols, creams, gels, patches, ointment, lotion, or foam.

The cosmetic composition may contain a wide variety of optional components, provided that such optional components are physically and chemically compatible with the essential components described herein. Examples of such components include those described in, e.g., U.S. Pat. No. 7,405,195; Harry's Cosmeticology, 7th Ed., Harry & Wilkinson (Hill Publishers, London 1982); Pharmaceutical Dosage Forms—Disperse Systems; Lieberman, Rieger & Banker, Vols. 1 (1988) & 2 (1989); Marcel Decker, Inc.; The Chemistry and Manufacture of Cosmetics, 2nd. Ed., deNavarre

3. Methods to Promote Expression of Pro-Angiogenic Factors, Decrease Anti-Angiogenic Factors and Fibrotic Factors The invention provides a method to promote expression of pro-angiogenic factors and decrease expression of anti-angiogenic factors in a cell comprising contacting a cell with an effective amount of IGFbp3. The invention further provides methods to also decrease the expression of fibrotic factors is a cell. The methods disclosed herein allow for the concurrent increased expression of pro-angiogenic factors and decreased expression of anti-angiogenic and fibrotic factors in a cell when contacted with an effective amount of IGFbp3.

The cells contacted with IGFbp3 are cells that have decreased expression of pro-angiogenic factors, and increased expression of anti-angiogenic and fibrotic factors. The cells are generally myocardial cells or monocytes.

Anti-angiogenic factors include without limitation, Thbs1, and Thbs4. A pro-angiogenic factor includes Angpt1. Fibrotic factors include without limitation factors that modulate collagen gene expression. One with ordinary skill in the art can determine anti-angiogenic, pro-angiogenic and fibrotic factors according to Table 2.

4. Methods to Promote Angiogenesis and Treat Cardiomyopathy

The invention provides a method to promote angiogenesis in a subject diagnosed with cardiomyopathy comprising administration to said subject an effective amount of IGFbp3. The IGFbp3 is generally an active form of the polypeptide.

The invention further provides a method to treat dilated cardiomyopathy in a subject in need of such treatment comprising administration to said subject an effective amount of IGFbp3.

To administer IGFbp3 to a subject, it is preferable to formulate the IGFbp3 in a composition comprising one or more pharmaceutically acceptable carriers.

The dose of the pharmaceutical composition of the present invention is determined according to the age, body weight, general health condition, sex, diet, administration time, administration method, clearance rate, and the level of disease for which patients are undergoing treatments at that time, or further in consideration of other factors. While the daily dose of the compound of the present invention varies depending on the condition and body weight of patient, the kind of the compound, administration route and the like, in regards to the type of administration, for example, 0.01 to 100 mg/patient/day.

Depending on the type of myopathy, the pharmaceutical compositions of the instant invention may be administered by routes independently selected from the group consisting of oral administration, intravenous administration, intraarterial administration, intramuscular administration, intracolonic administration, intracranial administration, intrathecal administration, intraventricular administration, intraurethral administration, intravaginal administration, subcutaneous administration, intraocular administration, intranasal administration, and any combinations thereof.

In the present specification, parenteral includes subcutaneous injection, intravenous injection, intramuscular injection, intraperitoneal injection, drip or topical administration (transdermal administration, transocular administration, transpulmonary or bronchial administration, transnasal administration, transrectal administration and the like) and the like.

Other types of cardiomyopathy include dilated cardiomyopathy, a condition in which the heart becomes weakened and enlarged, and it cannot pump blood efficiently, which includes common symptoms such as shortness of breath with activity or after lying down (or being asleep) for a while, swelling of feet and ankles (in adults), irregular or rapid pulse, fatigue, weakness, faintness, swollen liver, loss of appetite, cough, failure to thrive (in children), Need to urinate at night (in adults). Dilated cardiomyopathy can be the result of a genetic abnormality, congenital heart defect, damage from medicines such as chemotherapy, damage from drug use (such as alcohol or cocaine), damage from a prior infection or inflammation (myocarditis), damage from prior heart attacks or coronary artery abnormalities without limitation.

5. Methods to Promote Wound Healing

The invention provides a method to promote the healing of a wound comprising contacting wound with an effective amount of IGFbp3. "Wound" as used herein refers to any damage to any internal tissue of a subject or external injury (such as the epidermis) which may result in the loss of blood from the circulatory system and/or any other fluid from the patient's body. The tissue may be any mammalian internal tissue, such as an organ, including the heart, or blood vessel. A wound may be in a soft internal tissue, such as an organ, or in hard internal tissue, such as bone. The "damage" may have been caused by any agent or source, including traumatic injury, infection or surgical intervention. Thus, the "damage" being treated according to the methods of the present invention may be the result of either an accident or an intentional act. Wounded tissue also includes skin. "Wound healing" refers to the decrease in the time of wound recovery, and may include the associated capillary development required to heal the wounded tissue.

In certain embodiments of the invention, the wounded tissue is contacted by topical administration with a topical pharmaceutical composition comprising IGFbp3 and a pharmaceutically acceptable carrier. On with ordinary skill in the art can determine the effective amount of IGFbp3 required to treat a wounded by comparing the amount of time for the wound to heal compared to a wound being treated without IGFbp3.

In certain embodiments, a wound is contacted by topical administration with a topical pharmaceutical composition comprising IGFbp3 and a pharmaceutically acceptable carrier.

The topical composition is useful for treating wounded tissue, such as the skin. In addition, it is useful in regulating or improving skin condition, associated with skin inflammation, ageing, or other internal factors (e.g., biochemical changes from within the skin) or external factors (e.g., ultraviolet radiation, environmental pollution, wind, heat, low humidity, harsh surfactants, and abrasives).

In other embodiments the wound may be the heart, and the pharmaceutical composition comprising IGFbp3 and a pharmaceutically acceptable carrier may be contained in a hydrogel that is in contact with the heart, or myocardial tissue.

EXAMPLES

The invention now being generally described, it will be more readily understood by reference to the following examples, which are included merely for purposes of illustration of certain aspects and embodiments of the present invention, and are not intended to limit the invention.

Example 1

Methods and Materials

Methods

A mouse model of human dilated cardiomyopathy was generated by ablating the Id3 gene and a conditionally ablating the Id1 gene in the endothelium (Id conditional knockout or Id cKO mice). Postnatal cardiac phenotypes were observed. Id cKO mice that survived to adulthood exhibited fibrotic vasculature, cardiac enlargement and decreased cardiac function.

Mouse Colonies and Genotyping. Mice with a Flox insertion in the Id1 allele (Nam and Benezra, 2009) (generously provided by Drs. Nam and Benezra) and mice with a null mutation in the Id1 and Id3 genes were crossed to generate Id1F/FId3−/− or Id1F/—Id3−/− compound mice (referred as Id control mice). Tie2cre transgenic mice were subsequently crossed with Id control mice to generate Tie2cre+Id1F/FId3−/− and Tie2cre+Id1F/−Id3+/− mice (referred as Id cKO or Id1/3 cKO mice).

Both genotypes displayed the same phenotype. Mst1 transgenic mice. Mice were genotyped by PCR using puRe-Taq Ready-To-Go PCR beads (GE Healthcare) from DNA obtained from tail tips using primers for Id1 Flox, Id1 wild type, Id1 mutant, Id3 wild type, Id3 mutant and Tie2cre according to published protocols (Fraidenraich et al., 2004; Kisanuki et al., 2001; Nam and Benezra, 2009). R26LacZR26 mice, B6.129S4-Gt(ROSA)26Sortm1Sor/J, for verification of Cre/loxP-mediated recombination were purchased from The Jackson Laboratory.

Histology, immuno-, Xgal-staining and Western Blot (WB). Whole embryos were collected at embryonic day 11.5 (E11.5), E13.5, E15.5, E17.5 and whole hearts at postnatal day 1 (P1), P30, P60, P90 and P180. Placentas were collected at E17.5 Tissues were paraffin- or cryo-embedded and sectioned. Immunofluorescence was performed on paraffin sections using primary antibodies for Id1 (Biocheck), PECAM-1 (Santa Cruz), IGFbp3 (R&D) and Ki67 (abcam). Myosin heavy Chain MF20 (Developmental Studies Hybridoma Bank) was used to detect myogenic areas at embryonic and P1 and wheat germ agglutinin (WGA) was used to delineate cell membranes in adult hearts. Sections were pretreated with pressure cooker boiling for 5 minutes in citrate buffer (0.01M, pH 6.0, Polyscientifc), quenched of endogenous peroxidase in 3% $H_2O_2$, and blocked prior to primary antibody incubation. A biotin-streptavidin amplification procedure (Vector Labs) and tyramide signal amplification system (TSA) (Perkin Elmer) were used for Id1 and PECAM-1 staining while only biotin-streptavidin amplification was necessary for Ki67. Nuclei were identified with DAPI (Vector Labs). Visualization of fluorescence was performed using a Nikon Eclipse 80i microscope with NIS Elements Imaging Software. Nuclei positive for Ki67 were counted at 20× magnification at E13.5, E17.5, and P1 and divided by total number of nuclei to determine proliferation percentages.

ABBREVIATIONS

Vt: ventricle; At: atrium; AV EC: atrio-ventricular endocardial cushion, Tb: trabeculae; VS: ventricular septum; epic: epicardium; end: endocardium; Xgal: Xgalactosidase staining.

Hemotoxylin and Eosin staining was performed for morphological analysis and visualization of fibrosis was performed using Masson Trichrome Stain Kit (Richard-Allan Scientific). Whole mount X-gal staining was performed at E11.5 with X-gal (1 mg/mL) in PBS buffer containing 5 mM potassium ferricyanide, 5 mM potassium ferrocyanide, and 2 mM MgCl2 overnight at 37° C. X-gal wash buffer contained 0.02% Nonidet P-40. After staining embryos were cryo-embedded, sectioned and eosin counterstained before mounting. Adult hearts (p180) were harvested, cryo-embedded and sectioned before X-gal staining overnight at 37° C. and subsequent eosin counterstain.

Wound Healing. 6 WT and cKO (P60) mice were anesthetized by isoflurane inhalation. At time=0 days, two circular 7 mm-diameter wounds were inflicted using an Acupunch disposable sterile 7 mm skin biopsy punch (Accuderm Inc) and images were recorded. Wounds were dressed with a transparent dressing (Tegaderm; 3M) following initial wounding and again redressed at day 3. WT and cKO mice were sacrificed at day 6 and the remaining mice were sacrificed at day 8. Wounds with ~2 mm surrounding skin were excised at time of sacrifice and bisected to provide cross-sections through the full width of the wounds. These samples were fixed and processed for paraffin embedding and sectioned from both faces of the bisected tissue for histological analysis. H&E and immunofluorescence for ID1 and PECAM-1 were performed as described above. Semi qRT-PCR. RNA was extracted (RNeasy, QIAGEN) and 1 ug total RNA was reverse transcribed using Superscript III reverse transcriptase (Invitrogen). PCR was performed with the following primers and expected product size: Tbp1, GTCACATCGCCAACA-CAATC (SEQ ID NO. 1) and AGACCAAAGCCTGCAA-GAAA (SEQ ID NO. 2), 169 bp; Tbp4, GCAGGGATGG-TATTTGCACT (SEQ ID NO. 3) and TTCAGTCCCCAACTCCAAAC (SEQ ID NO. 4), 209 bp; Ang-1, TCTGCACAGTCTCGAAATGG (SEQ ID NO. 5) and AGGCTTGGTTTCTCGTCAGA (SEQ ID NO. 6), 204 bp; IGFBP3, AATGCTGGGAGTGTGGAAAG (SEQ ID NO. 7) and CTGTCTCCCGCTTAGACTCG (SEQ ID NO. 8), 193 bp; G3PDH primers (Clontech) for internal control, 983 bp. To produce bands in the log phase, PCR parameters were adjusted individually. Annealing temperatures: 55° C. 30 sec for Tbp1, Tbp4, Ang1 and 60° C. 30 sec for G3PDH; reaction cycle numbers: 24 for Tbp1; 29 for Tbp4 and Ang-1 and 22 for G3PDH.

IGFbp3 incubation. Hearts were harvested from Id cKO mice at P180. Adjacent, 1 mm thick transverse sections at mid-level were used for the experiment. One section was used for semi qRT-PCR without incubation. Two sections were incubated at 37° C. for 4 hours under rocking conditions in DMEM+1 mg/mL fatty acid-free BSA. Recombinant mouse IGFbp3 (1 µg/mL) (R&D Systems) was added to one section. No recombinant protein was added to another section (untreated control). Id cKO mice with EF<50% were used.

Experiments were performed in triplicate. For IGFbp3 antibody incubation, hearts were harvested from P180 WT mice. Adjacent, 1 mm-thick transverse sections at mid-level were used for the experiment. One section was used for semi qRT-PCR without incubation. Three sections were incubated at 37° C. for 5 hours under rocking conditions with DMEM and fatty acid-free BSA. An antibody reactive with IGFbp3 (80 µg/ml) (AF775, R&D Systems) was added to one section. No antibody was added to another section (untreated control). An unrelated antibody reactive with Fst1 (80 µg/ml)(K19, Santa Cruz) was added to another section (negative control). Both negative controls provided identical results. Experiments were performed in triplicate.

Myocyte cross-sectional area. Myocyte cross-sectional area was determined on digitized images of rhodamine-labeled wheat germ agglutinin-stained sections of paraffin embedded samples (Peter et al., 2007). Hearts from 6 WT (EF>60%) and 6 Id cKO (EF<50%) were used in this study. The myocyte outlines were traced and the cell areas measured with Image-Pro Plus (Media Cybernetics, Inc, Silver Spring, Md.). In cross sections of LV, the measurable cross sections of the myocytes are found in the endocardial one third and in epicardial one third of myocardium. At least 150 myocytes were routinely measured in each region.

Microarray analysis. 1 mm thick transverse sections at mid-level from 2 hearts per group (WT, Id1 KO, Id3 KO, Id cKO, IGFbp3-treated Id cKO and IGFbp3-untreated Id cKO) were used for microarray analysis. In the case of Id cKO groups, enlarged heart tissue from mice with EF<50% were collected. Sections used for microarrays were also used for semi qRT-PCR validation and were adjacent to those used for histology. Total RNA from heart tissue was isolated (RNeasy, QIAGEN). Gene expression was analyzed by the GeneChip Mouse Gene 1.0 ST Array (Affymetrix). Microarray data were processed by the RMA (robust multi-chip analysis) method, and expressed genes were selected by the detection above background (DABG) method. Hierarchical clustering with Pearson correlation was employed to cluster genes and samples using Cluster 3.0 and Tree View. Gene Ontology (GO) analysis was carried out by hypergeometric test. Significantly regulated genes used in GO analysis were those with expression change greater than 1× standard deviation of all genes. For each GO term, its associations with up- and downregulated genes were examined, resulting in two p-values. The more significant one was used to indicate the significance of the GO term. To report GO terms, we removed redundant ones, which contained more than 75% of genes associated with a GO term with higher significance. Data sets have been deposited in Gene Expression Omnibus (GEO), with accession number GSE21924.

Echocardiography. Echocardiographs were performed on WT, Id control and Id cKO mice at stages ranging from P30-P180 to determine left ventricular (LV) systolic fraction. Mice were anesthetized by intraperitoneal injection 2.5% Avertin 290 mg/kg. Transthoracic echocardiography (Sequoia C256; Acuson, Mountain View, Calif.) was performed using a 13-MHz linear ultrasound transducer. The chest was shaved. Mice were placed on a warm saline bag in a shallow left lateral position and warm coupling gel applied to the chest. Small-needle electrocardiographic leads were attached to each limb. Two-dimensional images and LV M-mode tracing (sweep speed=100-200 mm/s) were recorded from the parasternal short-axis view at the mid papillary muscle level. M-mode measurements of LV internal diameter (LVID) and wall thicknesses were made from consecutive beats and averaged using the leading edge-to-leading edge convention adopted by the American Society of Echocardiography. End-diastolic measurements were taken at the peak of R wave of EKG. End-systolic measurements were made at the time of the most anterior systolic excursion of the posterior wall. LV ejection fraction (EF) was calculated by the cubed methods as follows: LVEF (%)=100*[(LVIDd)3−(LVIDs)3]/(LVIDd)3, LV fractional shortening: (LVFS %)=100*(LVIDd−LVIDs)/LVIDd, where d indicates diastolic and s indicates systolic. Heart rate was determined from at least three consecutive RR intervals on the LV M-mode tracing. Following echocardiography at P180, mice were sacrificed and hearts harvested for histological analyses as described above.

Data analysis. Results are presented as mean±s.e.m. or as a range. Statistical comparison was performed with nonparametric two-tailed unpaired analysis of variance. A probability value of <0.05 was considered to be statistically significant.

Results

Id1 is compromised in the endothelial lineage of Id cKO hearts. To study a requirement for Id1 and Id3 genes in the adult heart, Id compound mice were analyzed with a Flox insertion in the Id1 allele and with a null mutation in the Id3 gene (Id1F/FId3−/− or Id1F/−Id3−/−, referred to as Id control) mice. A Tie2Cre transgene was incorporated into Id control mice to generate Tie2Cre+Id1F/FId3−/− or Tie2Cre+Id1F/−Id3−/− (referred to as Id cKO) mice. Tie2 is expressed in endothelial cells, which highly express Id genes. The Tie2 promoter, therefore, drives expression of the Cre recombinase to the endothelial and endothelial-derived structures.

To verify that the recombination was layer-specific, Tie2Cre+Id1F/+ mice were crossed to R26LacZR26 mice, which reveal tissues (via X-gal staining) that undergo Cre/loxP mediated recombination. The reporter LacZ showed that the recombination occurred in Tie2Cre+Id1F/+R26LacZR26 compound mice in most of the endocardial/endothelial cells and their derivatives like the atrio-ventricular endocardial cushion (AV EC). The epicardium and myocardium from atria and ventricles did not undergo recombination, and therefore did not stain blue. Accordingly, the epicardium was Id1 positive. Id1 was detected in the epicardium of both atria and ventricles, and in a few endothelial cells of the outer layer of the epi-myocardium. In contrast, negligible levels of Id1 were observed in endothelial cells of the inner most portion of the endomyocardium and of the VS, as well as of the endocardium proper. These observations suggest that Tie2Cre/LoxP-mediated recombination is more efficient in the inner myocardium, which is influenced by the endocardium, and may express higher levels of Tie2 (Cre).

Alternatively, a portion of the epi-endothelium may originate from endothelial independent structures (Tie2 negative=no Cre expression), such as from the epicardium. Thus, Tie2Cre/loxP-mediated recombination resulted in reduced Id1 production, especially in the most internal portions of the heart. Id1 persisted in a fraction of the endothelium of small capillaries and large vessels in the heart of WT mice at postnatal day 180 (P180), but did not persist in the epicardium or endocardium at P180. In Id cKO; R26LacZR26 compound mice, Tie2Cre/loxP-mediated recombination resulted in Xgal staining of the endothelial compartment, coincident with absence of Id1 staining there. Therefore, the only Id1-expressing cells in the WT heart are Tie2Cre+ cells, which are endothelial and endothelial-derived cells. Absence of Id1 in the epicardium and endocardium at P180, combined with Tie2Cre-ablation of Id1 in the endothelium leaves the heart of an adult Id cKO with no Id1 production.

Id cKO neonates develop a cardiac phenotype. The phenotypic consequences of Id loss in Id cKO embryos were examined. Embryos from crosses of Id cKO males and Id control females were generated. The two genotypes that form the Id cKO group produced identical phenotypes. Despite the fact that Tie2Cre/loxP-mediated recombination takes place as early as E11.5, and that Id1-endothelium expression is compromised in Id cKO embryos at E13.5 and E15.5, their hearts did not display a phenotype (n=25). At E13.5 (n=14) and E15.5 (n=11), the thickness of the myocardial wall of the Id cKO hearts did not differ from that of WT hearts, the trabeculation network was not compromised, the endothelial lining was continuous and the VS complete, with no VSDs. Concordant with normal size and thickness, no myocardial proliferation defects were apparent (n=3)(% Ki67 positive cells: 46±5 and 44±5 for WT and cKO respectively). These experiments suggest that partial (Tie2Cre+Id1F/−Id3−/− or Tie2Cre+Id1F/FId3−/−) but not complete (Id1−/−Id3−/−) absence of Id does not lead to midgestation demise. These experiments also suggest that Id1 signals from the non-endocardium/endothelium (i.e. epicardium and epicardial-derived structures) suffice for maintaining normal development of the embryonic heart. This is particularly interesting in areas of the heart that are internal and that do not appose the epicardium. These areas, like the VS, are devoid of short-range Id dependent signals, and yet, display no apparent phenotype at midgestation.

At E17.5, Id cKO hearts exhibited VSDs (n=15). The endocardial lining remained unaffected however a compromise in myocardial proliferation was observed (% Ki67 positive cells: 4.9±1.0 and 0.9±0.3 for WT and cKO respectively) (n=15 P<0.05). E17.5 embryos (n=33) were collected with no resorption sites. No change in apoptosis was observed (n=5). All the embryos showed beating hearts, including the Id cKO embryos (n=15, expected n=17). Because most of the Id cKO embryos survived past late gestation (88%, 15 out of 17 expected), the postnatal requirement of Id1-endothelium in the Id cKO pups was studied. Only 46% of the P1 Id cKO mice (56 out of 120 expected) escaped postnatal lethality. The phenotype of P1 Id cKO pups (n=11) was more pronounced to those of E17.5 embryos. The heart of the P1 Id cKO pups was enlarged (n=11) and displayed VSDs (n=11) associated with impaired ventricular trabeculation (n=11).

Trabeculae were surrounded by discontinuous endocardial cell lining. The VS contained one main hollow cavity, surrounded by a thin wall of VS myocytes. Red blood cells were observed within the VS cavity, suggesting a connection to the ventricular chambers. Accordingly, interruption of the precarious VS wall was apparent. The intramyocardial vasculature of the VS was dilated. In the VS, no difference in apoptosis was apparent (n=5), and negligible proliferation was observed (n=5)(% Ki67 positive cells: 2.3±1.0 and 0.5±0.3 for WT and cKO respectively, P<0.05). The epicardial vasculature displayed endothelial lining but was dilated. As expected, negligible levels of Id1 were observed in the heart of the Id cKO neonates.

Id cKO mice develop an adult cardiac phenotype. The requirement for Id genes in the adult heart of the surviving Id cKO mice at the functional and histological levels (n=56) were determined. At P30 (n=6), P60 (n=5), P90 (n=8) and P180 (n=28) the Id cKO mice did not display ventricular septal defects (VSDs) or trabeculation defects. The hearts of P1, P30, P60, P90 and P180 Id cKO mice were dilated (Table I). The heart/body (dry) weight ratio of the adult P180 cKO mice was 48% higher than that of WT mice (n=20)(Table I, P<0.05). The myocyte cross-sectional area of P180 Id cKO ([552±85]$\mu m^2$, n=6) was increased relative to WT ([314±17] $\mu m^2$, n=6)(P<0.01). The endo-myocardium of the left ventricle (LV)(apposing the Id negative endocardium) was disorganized, displayed areas with low or no cellularity and signs of fibrosis (n=14). The endocardium of the adult cKO mice was partially interrupted (n=8)(absence of CD31 positivity), with no visible endocardial nuclei (n=8).

Because the Id genes are not produced in the P180 endocardium, developmental ablation of Id genes may have had a long-term impact on the phenotype of the adult endocardium. Fibrotic tissue was apparent in areas surrounding large vessels (n=14) but their endothelial lining appeared normal (n=14). Fibrosis was not observed in the epimyocardium (n=14). This vascular-initiated pattern of fibrosis differed from that of another model in which the defect is triggered by myocardial apoptosis (n=5)(Yamamoto et al., 2003). The latter is exemplified by overexpression of the mammalian sterile 20 like-kinase 1 (Mst1) gene in the cardiac myocytes. As opposed to the Id cKO hearts, fibrosis in Mst1 Tg hearts was evenly distributed throughout the intercellular (interstitial) space of cardiac myocytes (n=5). The phenotype observed (a disorganized myocardium next to the endocardium) resembles that of the partially rescued Id dKO neonates with maternal injection of IGF1.

Monthly echocardiographic studies revealed that the left ventricular ejection fraction (LVEF) or fractional shortening (FS) of Id cKO mice was reduced (n=56)(Table I). The onset of heart dysfunction was at P90 (n=8). In the most severely affected Id cKO mice, LVEF was below 50% (Table I) (Id cKO EF: 21% and FS: 7.9%, compare with WT in EF: 64.7% and FS: 29.4%). Young pups (n=11)(P30 and P60) did not show low EF or FS readings. This suggests that the cardiac enlargement observed in young pups is compensatory for an intrinsic myocardial dysfunction. No significant difference in heart rate was observed at any stage (Table I). Control hearts from Tie2Cre+Id1F/−Id3+/− mice or other mice with higher Id copy number than Id cKO mice did not display enlargement, fibrosis, endocardial compromise or LVEF reduction. Thus, P180 Id cKO mice develop a vascular-initiated cardiac phenotype.

Analysis of Gene Expression Profiles.

The molecular consequences of conditional ablation of Id genes in the P180 heart were studied. Gene expression profiles were compared in clustering analysis. The effect of genetic modification in Id gene (Id1 KO, Id3 KO and Id1/3 cKO) was compared with the WT control heart. The sample clustering with relative gene expression levels revealed that the Id cKO heart has distinct pattern from the heart lacking either Id1 or Id3. The association of gene sets over the regulated genes using Gene Ontology (GO) database were evaluated. The significant GO terms (biological processes and cellular component) were summarized in heatmap with statistical scores. Id cKO showed strong regulation in cell adhesion (GO:0007155), actin filament-based process (GO: 0030029), vascular development (GO:0001944) and oxidation-reduction (GO:0055114). Those pathways are implicated in pathological cardiac remodeling. Id cKO also showed strong regulation in extracellular matrix (GO: 0031012) and extracellular region part (GO:0044421). The significant GO terms are listed in Table 2.

Vascular, fibrotic and hypertrophic markers are dysregulated in the adult Id cKO hearts. Microarray analysis of the extracellular matrix revealed that over 10 collagen genes were upregulated relative to WT, including types I (ID:12842) and III (ID:12825) (Table 2). Thrombospondin1 (Thbs1, ID:21825), a potent anti-angiogenic secreted factor, which is repressed by Id1, was upregulated in the Id cKO hearts relative to WT hearts (Table 2). Thbs4 (ID: 21828) was also upregulated (Table 2). Several Thbs-carrying domain proteins, like a disintegrin-like and metallopeptidase with thrombospondin (Adamts4, 9 and 1, IDs: 240913, 101401 and 11504 respectively) proteins, were also up-regulated (Table 2). Adamts proteins play key roles in extracellular matrix remodeling, including degradation of collagen fibers. Angiopoietin-1 (Angpt1, ID: 11600), a secreted factor produced by myocytes that signals to the endocardium through the Tie2 receptor and whose absence during development leads to trabeculation defects, was down-regulated (Table 2) in the Id cKO hearts. As in the phenotype of Id dKO embryos, lack of Angpt1 causes embryonic lethality at midgestation and a thin myocardium. Thus, important paracrine signals of the cardiac vasculature are dysregulated in the Id cKO adult hearts. In the Id dKO embryos, IGF1 (ID: 16000) and IGFbp4 (ID: 16010) were down- and up-regulated respectively (Fraidenraich et al., 2004). However, IGF1 and IGFbp4 were unchanged in the Id cKO adult hearts. Instead, IGFbp-3, 5 and 7 (IDs: 16009, 16011 and 29817 respectively) were upregulated (Table 2). In P180 WT hearts, IGFbp3 was detected in a few small-caliber (nonmyocardial) cells that appose larger cardiac myocytes. IGFbp3 was also detected in the endothelial lining of larger vessels. Concordant with upregulation of IGFbp3 (Table 2), IGFbp3 was enhanced in the P180 Id cKO hearts, to become detectable throughout the extracellular interstitium. Therefore, IGFbp3 is expressed primarily in the nonmyocardial compartment, including endothelial cells, and its expression is enhanced in the P180 Id cKO heart.

Microarray analysis of markers of hypertrophy revealed that atrial and brain natriuretic precursor peptides (Nppa or ANF and Nppb or BNF, IDs: 230899 and 18158), were upregulated relative to WT (Table 2). The developmental Myh7 gene (β-MHC, ID: 140781) was also upregulated while the adult Myh6 (α-MHC, 17888) was unchanged, suggesting an isozyme shift of MHC expression (Table 2). As expected, Id1 and Id3 (ID: 15901 and 15903 respectively) were both downregulated relative to WT (Table 2). Loss of Id1 in the Id cKO heart was further confirmed by semi qRT-PCR and Western blot. Id4 (ID: 15904), which is not expressed and may not play a role in the heart, was unchanged (Table 2). However, Id2 (ID: 15902), whose pattern of expression and function overlaps with those of Id1 and Id3, was slightly upregulated (Table 2), suggesting a modest compensatory mechanism between members of the Id family. As expected, hearts from Tie2Cre+Id1−/−Id3+/− and Id1F/+Id3−/− mice, which contain higher Id levels than those from Id cKO mice, did not reveal severe changes in gene expression profiles (Table 2). The gene expression studies provide a panel of vascular, fibrotic and hypertrophic markers that are altered in the hearts of Id cKO mice.

Reversion of vascular and fibrotic, but not hypertrophic markers in IGFbp3-treated Id cKO heart explants. Because Id and IGFbp3 are expressed in the endothelial compartment, Id represses IGFbp3, and the IGF axis plays a role in the rescue of Id KO embryos, it was determined whether IGFbp3 plays a role on the reversion of gene expression profiles in Id cKOs. To this end, transverse sections of P180 Id cKO hearts were incubated in the presence and absence of mouse recombinant IGFbp3. In this condition, the potential interactions between the multiple layers (myocardium-epicardium-endocardium-endothelium) remain intact. It was determined that IGFbp3 treatment reversed expression of genes dysregulated in Id cKO. Notably, an opposite regulation was apparent in genes that belong to the extracellular matrix and extracellular region part (GO:0031012 and GO:0044421 respectively, compare Id1/3 cKO with IGFbp3 treated).

IGFbp3 treatment reversed expression profiles of specific members of the vascular and fibrotic pathways (Table 2). The anti-angiogenic Thbs4 and Thbs1 were downregulated by IGFbp3 addition (Table 2). According to this observation, Id dependent, anti-angiogenic Thbs family can be normalized by IGFbp3 administration. Conversely, expression of the pro-angiogenic Angpt1 was up-regulated by IGFbp3 addition (Table 2). Thus, IGFbp3 promotes expression of pro-angiogenic markers and represses expression of anti-angiogenic markers in Id cKO hearts. Regarding key components of the fibrotic tissue, a direct effect on specific expression of 2 collagen genes was observed (type I and type XV, IDs: 12842 and 12819 respectively, (Table 2). Despite the fact that Thbs1/4 were affected, none of the Adamts (4, 9 and 1) proteins, which contain a Thbs domain, were changed by IGFbp3 addition (Table 2). Surprisingly, however, no direct effect of IGFbp3 was observed on the regulation of hypertrophic markers, like ANF, BNF or βMHC (Table 2). Id2 expression was not affected by IGFbp3 administration (Table 2). Similarly, no effect on IGFbp 3, 5 and 7 was observed. However, IGFbp4 was down-regulated (Table 2), suggesting a compensatory cross-talk among members of the IGFbp family. We also incubated transverse sections of WT hearts in the presence of an antibody reactive with IGFbp3. The treatment resulted in Thbs4/1 upregulation and Angpt1 downregulation. As expected, this outcome in WT with IGFbp3 antibody (dysregulation) was opposite to that in Id cKO with recombinant IGFbp3 (reversion). The experiments suggest that addition of recombinant IGFbp3 in Id-deficient hearts is corrective, and that a block of IGFbp3 mimics the effect produced by Id-deficiency.

Vascular compromise takes place outside the heart. Because the vascular-specific recombination of Id1 was not restricted to the heart, it was determined whether endothelial ablation of Id1 also led to angiogenic defects outside of the heart. To this end, P60 Id cKO (n=6) or WT (n=6) mice were subjected to excisional skin wounding (n=12, 2 wounds per mouse), and the wound healing response was studied over a period of 8 days. Wound closure was markedly delayed in the Id cKO relative to WT. Accordingly, histopathological examination revealed a defective angiogenesis. Overall, granulation tissue formation was less dense at the Id cKO border zone of the wound (relative to WT). At day 6, a burst of small, Id-positive endothelial capillaries, accompanied by extensive granulation, emerged from the uninjured skin towards the injured skin at the border zone, underneath a region of new epithelium. However, in the wounds of the Id cKO mice, granulation was markedly less dense. Consistent with almost complete loss of wound healing activity, capillary development was sparse. By day 8, the wounds were largely healed in WT mice, but the wounds in the Id cKO mice were still unhealed. At the histological level, less cellularity or hypoplasticity was apparent in the Id cKO mice. Strikingly, a network of large caliber and distended (Id-negative) vessels was prevalent in the Id cKO wound. Thus, this experiment supports the notion that the Id cKO mice have a compromised angiogenic response to external injury.

TABLE 1

Cardiac dilation, fibrosis and dysfunction in P180 Id cKO mice

|  | WT | Id cKO |
|---|---|---|
| Body weight (g)* | | |
| Females | 26.2 ± 2.6 (n = 6) | 22.3 ± 2.6 (n = 30) |
| Males | 29.3 ± 2.2 (n = 9) | 24.3 ± 2.4 (n = 24) |
| Heart weight (mg)†# | | |
| Females | 105 ± 16 (n = 6) | 118 ± 26 (n = 9) |
| Males | 118 ± 23 (n = 5) | 140 ± 38 (n = 11) |
| Heart/Body weight (mg/g)* | 3.87 ± 0.62 (n = 11) | 5.75 ± 1.10 (n = 20) |
| Fibrosis (Masson Trichrome staining) | | |
| Epimyocardium | 0 (n = 5) | 0 (n = 14) |
| Endomyocardium | 0 (n = 5) | 12 (n = 14) |
| Left Ventricular End Diastolic Dimension (LVEDD)* | | |
| mm | 3.8 ± 0.3 (n = 14) | 4.3 ± 0.7 (n = 56) |
| Left Ventricular End Systolic Dimension (LVESD)* | | |
| mm | 2.7 ± 0.3 (n = 14) | 3.3 ± 0.7 (n = 56) |
| Fractional Shortening (FS)* | | |
| % | 29.4 ± 4.6 (n = 14) | 23.3 ± 7.0 (n = 56) |
| Left Ventricular Ejection Fraction (LVEF)* | | |
| % | 64.3 ± 6.8 (n = 14) | 56.2 ± 13.2 (n = 56) |
| Number of mice with LVEF < 50 % | 0 (n = 14) | 11 (n = 56) |
| Heart rate (HR)† | | |
| Beats/min (bpm) | 450 ± 55 (n = 14) | 440 ± 62 (n = 56) |

*P < 0.05
†P > 0.05
In parenthesis: number of mice
dry weight

TABLE 2

| GO ID, term | Id1KO | Id3KO | Id1/3cKO | Igfbp3-treated Id1/3cKO |
|---|---|---|---|---|
| Biological Process | | | | |
| GO:0007155, cell adhesion | 9.79 | 8.06 | 21.59 | −2.05 |
| GO:0007606, sensory perception of chemical stimulus | −18.04 | −11.90 | −0.80 | −3.43 |
| GO:0030029, actin filament-based process | 0.83 | 3.00 | 15.55 | −0.45 |
| GO:0001944, vasculature development | 2.40 | 2.27 | 15.10 | −3.08 |
| GO:0006928, cell motion | 3.01 | 4.13 | 14.65 | −1.02 |
| GO:0048513, organ development | 4.83 | −2.92 | 14.31 | −4.86 |
| GO:0009605, response to external stimulus | 8.24 | 4.97 | 12.84 | −2.12 |
| GO:0002376, immune system process | −1.59 | 5.21 | 12.06 | −1.88 |
| GO:0007167, enzyme linked receptor protein signaling pathway | 4.08 | 2.98 | 10.07 | −2.41 |
| GO:0006396, RNA processing | 0.07 | 0.08 | 0.00 | 9.72 |
| GO:0051186, cofactor metabolic process | −0.46 | −0.14 | −9.39 | 0.24 |
| GO:0030154, cell differentiation | −1.23 | −0.95 | 9.17 | −5.88 |
| GO:0055114, oxidation reduction | 1.24 | −0.23 | −9.02 | 0.32 |
| GO:0006952, defense response | 2.35 | −3.82 | 8.46 | −2.60 |
| GO:0008283, cell proliferation | 1.80 | 1.13 | 7.92 | −4.09 |
| GO:0044255, cellular lipid metabolic process | 2.57 | 0.15 | −7.78 | −0.10 |
| GO:0006366, transcription from RNA polymerase II promoter | −0.48 | −1.61 | 0.64 | −7.44 |
| GO:0019752, carboxylic acid metabolic process | 1.97 | −0.41 | −7.27 | 0.32 |
| GO:0006811, ion transport | 5.30 | 6.94 | −2.86 | −2.20 |
| GO:0050793, regulation of developmental process | −1.23 | −3.32 | 6.94 | −1.81 |
| GO:0043062, extracellular structure organization | 5.48 | 1.96 | 6.77 | −0.79 |
| GO:0051258, protein polymerization | 1.34 | 0.67 | 5.66 | −0.28 |
| GO:0006412, translation | −0.03 | −0.39 | 0.00 | 5.13 |
| GO:0009890, negative regulation of biosynthetic process | −0.03 | −0.10 | 0.28 | −5.03 |
| GO:0030705, cytoskeleton-dependent intracellular transport | −0.58 | 0.28 | 4.75 | −0.42 |
| GO:0048518, positive regulation of biological process | −0.81 | −4.74 | 3.96 | −3.39 |
| GO:0065008, regulation of biological quality | 4.73 | −1.81 | 3.87 | −0.32 |
| GO:0048519, negative regulation of biological process | −0.55 | −0.85 | 2.48 | −4.40 |
| GO:0006776, vitamin A metabolic process | 0.88 | −1.63 | −4.14 | 0.32 |
| GO:0043407, negative regulation of MAP kinase activity | 1.18 | 3.97 | 0.87 | −0.55 |
| GO:0043623, cellular protein complex assembly | 0.90 | −0.36 | 3.87 | 0.09 |
| GO:0006766, vitamin metabolic process | 0.38 | −1.01 | −3.62 | −0.12 |
| GO:0032963, collagen metabolic process | 2.64 | 0.72 | 3.59 | −0.44 |
| GO:0016055, Wnt receptor signaling pathway | 0.31 | −0.16 | 0.69 | −3.52 |
| GO:0007242, intracellular signaling cascade | 0.69 | 0.80 | 3.49 | −0.27 |
| GO:0015669, gas transport | −1.34 | −3.42 | −2.02 | −0.31 |
| GO:0006259, DNA metabolic process | 0.00 | 0.25 | −0.02 | 3.38 |
| GO:0006461, protein complex assembly | 1.27 | −0.40 | 3.32 | 0.34 |
| GO:0051128, regulation of cellular component organization | −0.46 | −0.52 | 3.24 | −0.19 |
| GO:0015849, organic acid transport | 2.23 | 1.87 | −0.53 | −3.22 |
| GO:0002009, morphogenesis of an epithelium | −0.46 | −0.62 | 3.22 | −0.91 |
| GO:0010033, response to organic substance | −1.63 | −3.19 | −0.74 | −0.49 |
| GO:0009790, embryonic development | 0.45 | 1.20 | 2.84 | −3.18 |
| GO:0006511, ubiquitin-dependent protein catabolic process | −0.02 | 0.20 | 0.03 | 3.10 |
| GO:0042221, response to chemical stimulus | −1.87 | −3.00 | 1.80 | −1.16 |
| GO:0006950, response to stress | 0.90 | −2.34 | 2.99 | −0.39 |
| GO:0007292, female gamete generation | −0.90 | 1.17 | −2.95 | 0.52 |
| GO:0007626, locomotory behavior | −2.94 | 2.47 | 1.87 | −0.43 |
| GO:0034660, ncRNA metabolic process | 0.04 | 0.51 | −0.01 | 2.94 |
| GO:0008643, carbohydrate transport | 2.83 | 1.62 | −1.12 | −0.73 |
| GO:0043086, negative regulation of catalytic activity | 0.46 | −2.82 | 1.18 | −0.83 |
| GO:0016265, death | −0.12 | −1.74 | 2.81 | −0.68 |
| GO:0007610, behavior | −2.80 | 1.88 | 2.16 | −0.69 |
| GO:0006508, proteolysis | 1.55 | 1.18 | 0.76 | 2.79 |
| GO:0009308, cellular amine metabolic process | 0.92 | −1.09 | −2.79 | 0.34 |
| GO:0006790, sulfur metabolic process | 0.35 | −0.52 | −2.79 | −0.43 |
| GO:0048511, rhythmic process | −0.35 | −2.71 | 1.47 | −0.54 |
| GO:0016044, membrane organization | 1.54 | 0.31 | 2.69 | −0.19 |
| GO:0051239, regulation of multicellular organismal process | 2.65 | 0.94 | 1.93 | −0.75 |
| GO:0034330, cell junction organization | 1.34 | 1.28 | 2.65 | −1.04 |
| GO:0065009, regulation of molecular function | 0.53 | 1.82 | 2.60 | 0.39 |
| GO:0015844, monoamine transport | −1.11 | −0.34 | −2.59 | −0.26 |
| GO:0007010, cytoskeleton organization | −0.38 | −0.49 | 2.53 | 0.33 |
| GO:0019748, secondary metabolic process | 0.65 | −2.34 | −2.37 | 1.42 |
| GO:0042254, ribosome biogenesis | 0.44 | 0.20 | −0.01 | 2.37 |
| GO:0009966, regulation of signal transduction | 0.61 | 0.79 | 2.35 | −0.93 |
| GO:0022613, ribonucleoprotein complex biogenesis and assembly | 0.19 | 0.26 | 0.00 | 2.32 |
| GO:0006800, oxygen and reactive oxygen species metabolic process | −0.12 | −2.29 | 1.22 | 0.94 |
| GO:0040007, growth | 1.97 | −0.58 | 2.29 | −0.42 |
| GO:0006725, cellular aromatic compound metabolic process | −1.68 | −2.17 | −0.85 | 0.43 |
| GO:0006066, cellular alcohol metabolic process | 0.89 | −0.54 | −2.11 | −0.73 |
| GO:0046148, pigment biosynthetic process | 0.96 | −0.48 | −2.10 | 0.74 |

TABLE 2-continued

| GO ID, term | Id1KO | Id3KO | Id1/3cKO | Igfbp3-treated Id1/3cKO |
|---|---|---|---|---|
| GO:0007219, Notch signaling pathway | 0.51 | −0.11 | 2.04 | −0.54 |
| GO:0006468, protein amino acid phosphorylation | 0.20 | 0.55 | 2.03 | −0.43 |
| GO:0007569, cell aging | 0.23 | 0.09 | 2.01 | −0.82 |
| Cellular Component | | | | |
| GO:0031012, extracellular matrix | 39.44 | 9.51 | 35.10 | −5.42 |
| GO:0044421, extracellular region part | 33.46 | 5.23 | 31.44 | −7.33 |
| GO:0044459, plasma membrane part | 0.63 | 6.10 | 16.59 | −1.76 |
| GO:0005739, mitochondrion | −0.49 | 0.00 | −16.01 | 0.02 |
| GO:0005856, cytoskeleton | 0.43 | 0.98 | 15.58 | −0.25 |
| GO:0030529, ribonucleoprotein complex | −0.02 | −0.25 | 0.00 | 9.19 |
| GO:0042995, cell projection | −0.54 | 1.24 | 8.20 | −1.25 |
| GO:0005783, endoplasmic reticulum | 6.30 | 2.38 | −0.24 | 0.15 |
| GO:0044445, cytosolic part | −1.21 | −0.83 | −0.66 | 4.33 |
| GO:0043228, non-membrane-bounded organelle | −0.04 | 0.24 | 4.12 | 2.39 |
| GO:0031967, organelle envelope | −0.45 | −0.02 | −3.69 | 0.22 |
| GO:0031090, organelle membrane | −0.13 | −0.01 | −3.60 | 0.09 |
| GO:0044428, nuclear part | 0.00 | 0.00 | 0.00 | 3.60 |
| GO:0005777, peroxisome | 0.15 | 0.06 | −3.46 | 0.18 |
| GO:0005938, cell cortex | 0.69 | 0.92 | 3.27 | 0.53 |
| GO:0005794, Golgi apparatus | 3.13 | 0.51 | 0.20 | 0.28 |
| GO:0043292, contractile fiber | 1.51 | 2.34 | 2.56 | 0.51 |
| GO:0019898, extrinsic to membrane | 0.83 | 1.33 | 2.12 | 0.15 |
| GO:0005829, cytosol | −0.20 | −0.91 | −0.27 | 2.03 |
| GO:0005624, membrane fraction | 1.92 | 2.02 | 0.92 | 1.18 |

The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. All publications U.S. Patents, references and GenBank sequences cited in this disclosure are incorporated by reference in their entireties. The citation of any references herein is not an admission that such references are prior art to the present invention.

Those skilled in the art will recognize, or be able to ascertain using no more than routine experimentation, many equivalents to the specific embodiments of the invention described herein. Such equivalents are intended to be encompassed by the following embodiments.

What is claimed is:

1. A method to promote angiogenesis in a subject diagnosed with cardiomyopathy comprising administering to said subject an effective amount of Insulin-like Growth Factor binding protein-3 (IGFbp3).

2. The method of claim 1, wherein said cardiomyopathy is dilated cardiomyopathy.

3. A method to treat cardiomyopathy in a subject in need of such treatment comprising administering to said subject an effective amount of IGFbp3.

4. The method of claim 3, wherein said cardiomyopathy is dilated cardiomyopathy.

* * * * *

SEQUENCE LISTING

```
<160> NUMBER OF SEQ ID NOS: 8

<210> SEQ ID NO 1
<211> LENGTH: 20
<212> TYPE: DNA
<213> ORGANISM: ARTIFICIAL
<220> FEATURE:
<223> OTHER INFORMATION: SYNTHETIC PRIMER

<400> SEQUENCE: 1
gtcacatcgc caacacaatc                                              20

<210> SEQ ID NO 2
<211> LENGTH: 20
<212> TYPE: DNA
<213> ORGANISM: ARTIFICIAL
<220> FEATURE:
<223> OTHER INFORMATION: SYNTHETIC PRIMER

<400> SEQUENCE: 2
agaccaaagc ctgcaagaaa                                              20

<210> SEQ ID NO 3
<211> LENGTH: 20
<212> TYPE: DNA
<213> ORGANISM: ARTIFICIAL
<220> FEATURE:
<223> OTHER INFORMATION: SYNTHETIC PRIMER
```

```
-continued

<400> SEQUENCE: 3
gcagggatgg tatttgcact                                            20

<210> SEQ ID NO 4
<211> LENGTH: 20
<212> TYPE: DNA
<213> ORGANISM: ARTIFICIAL
<220> FEATURE:
<223> OTHER INFORMATION: SYNTHETIC PRIMER

<400> SEQUENCE: 4
ttcagtcccc aactccaaac                                            20

<210> SEQ ID NO 5
<211> LENGTH: 20
<212> TYPE: DNA
<213> ORGANISM: ARTIFICIAL
<220> FEATURE:
<223> OTHER INFORMATION: SYNTHETIC PRIMER

<400> SEQUENCE: 5
tctgcacagt ctcgaaatgg                                            20

<210> SEQ ID NO 6
<211> LENGTH: 20
<212> TYPE: DNA
<213> ORGANISM: ARTIFICIAL
<220> FEATURE:
<223> OTHER INFORMATION: SYNTHETIC PRIMER

<400> SEQUENCE: 6
aggcttggtt tctcgtcaga                                            20

<210> SEQ ID NO 7
<211> LENGTH: 20
<212> TYPE: DNA
<213> ORGANISM: ARTIFICIAL
<220> FEATURE:
<223> OTHER INFORMATION: SYNTHETIC PRIMER

<400> SEQUENCE: 7
aatgctggga gtgtggaaag                                            20

<210> SEQ ID NO 8
<211> LENGTH: 20
<212> TYPE: DNA
<213> ORGANISM: ARTIFICIAL
<220> FEATURE:
<223> OTHER INFORMATION: SYNTHETIC PRIMER

<400> SEQUENCE: 8
ctgtctcccg cttagactcg                                            20
```